United States Patent [19]
Van Steenburg

[11] Patent Number: 4,912,754
[45] Date of Patent: Mar. 27, 1990

[54] X-RAY PATIENT SUPPORT APPARATUS
[75] Inventor: Kip P. Van Steenburg, Sudbury, Mass.
[73] Assignee: John K. Grady, Littleton, Mass.
[21] Appl. No.: 797,633
[22] Filed: Nov. 13, 1985
[51] Int. Cl.[4] ............................................... A61B 6/04
[52] U.S. Cl. .................................... 378/209; 378/179; 378/195; 378/196; 269/323
[58] Field of Search ............... 269/108, 322, 323, 325; 128/653; 378/177, 179, 195–198, 20, 209, 147

[56] References Cited
U.S. PATENT DOCUMENTS

| | | | |
|---|---|---|---|
| 2,172,941 | 9/1939 | Manning et al. | 269/325 |
| 3,281,598 | 10/1966 | Hollstein | 378/196 |
| 3,778,049 | 12/1973 | Viamonte, Jr. | 378/209 |
| 3,843,112 | 10/1974 | McDonald | 269/322 |
| 3,927,326 | 12/1975 | Kunne et al. | 378/179 |
| 4,426,725 | 1/1984 | Grady | 378/196 |
| 4,540,165 | 9/1985 | Green et al. | 269/325 |

FOREIGN PATENT DOCUMENTS 2126312  12/1972  Fed. Rep. of Germany ...... 378/179

Primary Examiner—Craig E. Church
Assistant Examiner—John C. Freeman
Attorney, Agent, or Firm—James H. Grover

[57] ABSTRACT

An X-ray table top is moveably supported by a shaft extending from a support mechanism on a base to the end of the table top at one longitudinal side thereof offset from the longitudinal axis of the top. The support mechanism includes means for raising and lowering the table top, Trendelenburg tilting the top about an axis transverse of its longitudinal axis and canting it about the longitudinal axis or an axis parallel thereto. The offset support connection to the table top allows unobstructed access to both sides, the foot end, and to the head end of the table top for anesthesiological personnel and equipment.

5 Claims, 4 Drawing Sheets

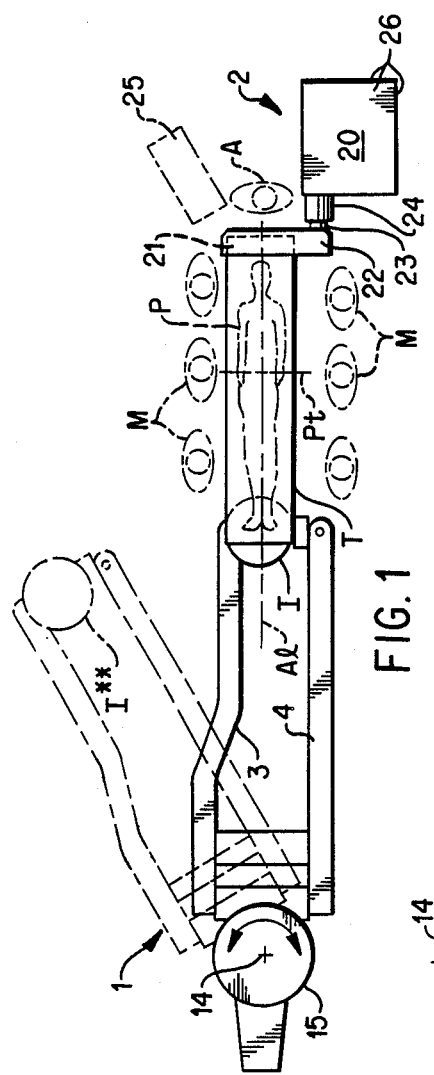
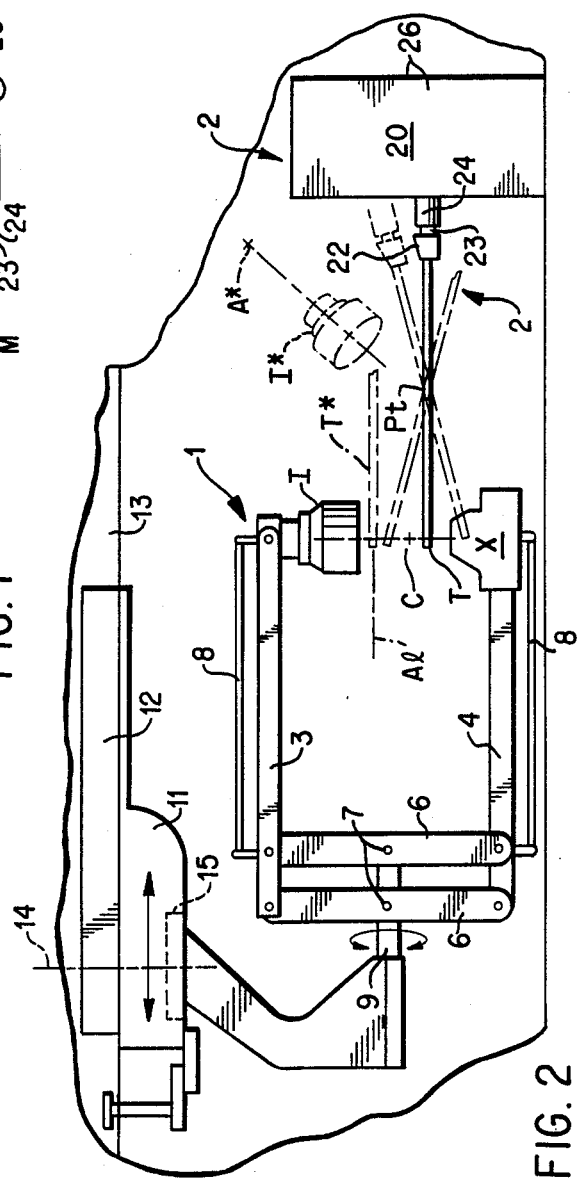
FIG. 1
FIG. 2

X-RAY PATIENT SUPPORT APPARATUS

BACKGROUND OF THE INVENTION

This invention is concerned with the use of X-ray images of a patient during medical procedures such as surgery, catheterization and dye angiography during which a patient lying on a table is treated by a team typically of physicians, nurses and an anesthesiologist around the table who are guided by a display of X-ray images produced by an X-ray tube and receptor such as an image intensifier. X-ray apparatus has been developed as shown in United States Pat. Nos. 3,892,967 and 4,426,725, which can image any part of a patient from head to foot and at nearly any spherical angle. But space must be allowed for an X-ray tube and receptor set to move in and out of unlimited positions in a zone around the full length of the patient, and to rotate about the longitudinal, head to foot, axis of the patient and table. Moreover the medical team must have ready access to the patient not only from the longitudinal sides of the table, but also at the head and foot. The anesthesiologist and equipment are at the head of the patient table, the physicians and nurses are at both sides of the table and circulate around the foot of the table.

Various attempts have been made to provide a table which will accommodate the needs of access by the physicians and nurses concomitantly with the need to move the radiation axis between the X-ray tube and receptor set in the zone. Table tops have been translatively mounted on a base column to slide into the radiation axis, but the consequent movement of the patient results in serious problems for the anesthesiologist who must prevent many supporting tubes, hoses and monitoring lines from being tangled, kinked or pulled loose from the patient. If the table is supported on a fixed pedestal at the head of the patient it will either interfere with the anesthesiologist work or obstruct radiological examination of the head end of the patient. If the pedestal is at the foot or middle of the table it will prevent the necessary movement of the X-ray tube and receptor set in the zone. If the table pedestal is at either of the longitudinal sides of the table radiology is more seriously obstructed and also interferes with the needed full and comfortable access by the attending medical team.

The prior side or end support of the patient table is unsatisfactory not only for the above reasons but also because it does not allow for lifting and rotation of the table top, particularly Trendelenburg tilting of a patient in trauma about an axis transverse of the longitudinal patient and table axis at the middle of the table.

Accordingly it is one object of the present invention to support a patient table top in a way which will not interfere with access of the medical team to, and circulation around, the patient and which allows unobstructed access below the patient at the head of the table in addition to allowing entrance of the X-ray source and receptor set to diametrically opposed sides of the table top.

Further objects are to provide the table top with movements including Trendelenburg tilting without sacrificing full access of the medical team and X-ray apparatus to the patient.

SUMMARY OF THE INVENTION

According to the invention apparatus for supporting a patient during medical procedures comprises a table top for a patient having a longitudinal axis through the head and foot ends of the top; a support for the table top including a base and mechanism for moveable support of the table; and a support connection between the support mechanism and one end of the table top, the connection extending and joining to the table top at one longitudinal side thereof offset from the longitudinal axis and providing at the supported end of the table top an area of unobstructed access to medical personnel.

Further according to the invention the support mechanism has means for canting the table top, that is, rotating the top about its longitudinal axis and means for tilting the table top, that is, rotating the table top about an axis transverse of its longitudinal axis.

In one specific aspect the support means includes an arm connected to one end of the table top and extending laterally thereof, and a rotating shaft connected to the arm offset from the longitudinal axis of the top on a rotation axis parallel to and offset from the longitudinal axis of the table top.

In still a further aspect the patient support apparatus is in combination with radiological apparatus including a two-armed stand with a radiation source and a radiation receptor on respective arms moveable into a radiology zone around the longitudinal axis of the table top.

DRAWINGS

FIGS. 1 and 2 are a plan view and side elevation of patient support apparatus in combination with radiological apparatus according to the invention;

DESCRIPTION

Figure 3:
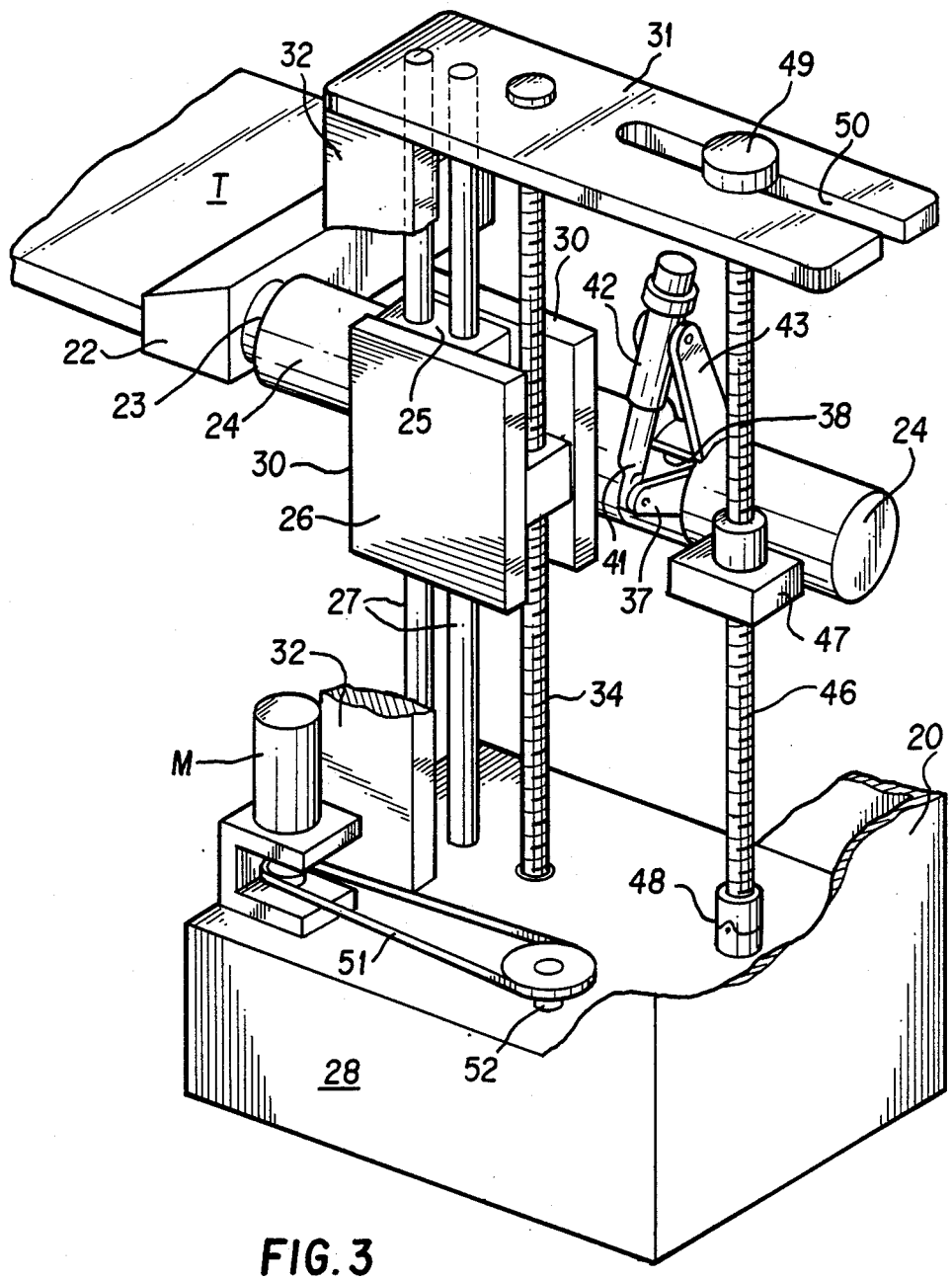
FIG. 3 is an isometric view of the patient support apparatus partly broken away.

In FIGS. 1 and 2 a patient P on the table top T of support apparatus 2 is located in the operating room of a hospital in conjunction with X-radiological apparatus 1.

The radiological apparatus 2, described more fully in United States Pat. Nos. 3,892,967 and 4,426,725, has two arms 3 and 4 respectively carrying a radiation set including an X-ray tube X and an X-ray receptor and image intensifier I electrically connected to a CRT display, not shown. The tube and receptor are held on radiation axis A1. The arms 3 and 4 are mounted in parallelogram form on cross members 6 with pivots 7 and tie rods 8 allowing reshaping the parallelogram so that the radiation axis as one side of the parallelogram is angulated about an isocenter C to view the patient from angles of over 90° in longitudinal planes through longitudinal axis Al of the table T and the patient P. Additionally, the cross bars 6, 7 can turn with an axle 9 allowing the radiation set to be rotated 360° through a cylindrical zone around the patient and the longitudinal axis Al. The combination of parallelogram angulation and rotation on the axle 9 allows radiography from most loci on a sphere about a point in the body of the patient. Still further movement of the radiation axis linearly along the table axis is afforded by suspending the axle from a carriage 11 riding in a track 12 in the ceiling 13 of the operating room. The phantom position I* of the image intensifier illustrates the longitudinal movement and angular adjustment of the parallelogram together with rotation of the parallelogram on the angle 9. It will be understood that the X-ray tube is moved complementarily to the image intensifier I so that the tube remains on the radiation axis in its adjusted position Ax*.

The patient support 2 of FIGS. 1 and 2, shown in detail in FIGS. 3 to 6, comprises the table top T and an upright housing 20 containing mechanism for moveable support of the table. The table top is partly or preferably wholly made of an X-radiationtranslucent material such as carbon fibre. A lateral arm 21 extends away from the longitudinal axis Al to an offset portion 22 at or preferably outside one longitudinal side 23 of the table top. At the offset portion 22 the arm is connected to a shaft 23. The shaft 23 is journalled in a bearing tube 24 supported by the mechanism of the housing 20.

As shown in FIG. 1 the connection between the table top T and support mechanism in the housing 20 leaves an area at the head end of the patient table unobstructed. The anesthesiologist A has direct, unimpeded access to the head of the patient for personal attention and for the supporting tubes, hoses and vital function monitoring lines extending between the patient's head and body to the adjacent equipment table 26. The anesthesiologist and complex equipment need not be disturbed during the medical procedure on the table because the patient support 2 remains stationary while the radiological parallelogram 1 moves over and around the patient. The medical team M has free access to both longitudinal sides of the table. And, when the X-ray apparatus is retracted to the lateral phantom position I** of the image intensifier in FIG. 2, the medical team can change individual positions by circulation around the foot end of the table.

The patient support as described above not only provides significantly freer access to the patient during surgical procedures than hitherto, but at the same time allows freedom for movement of the X-ray equipment visually supporting the medical procedure. The cylindrical zone along and around the patient and table top is clear for entrance and movement of the X-ray tube X and image intensifier I above and below in all positions on opposite sides of the longitudinal axis Al of the patient and table. Because the table top T and its lateral arm 21 are X-ray-translucent the patient can be completely monitored visually from all useful angles.

Figure 4:
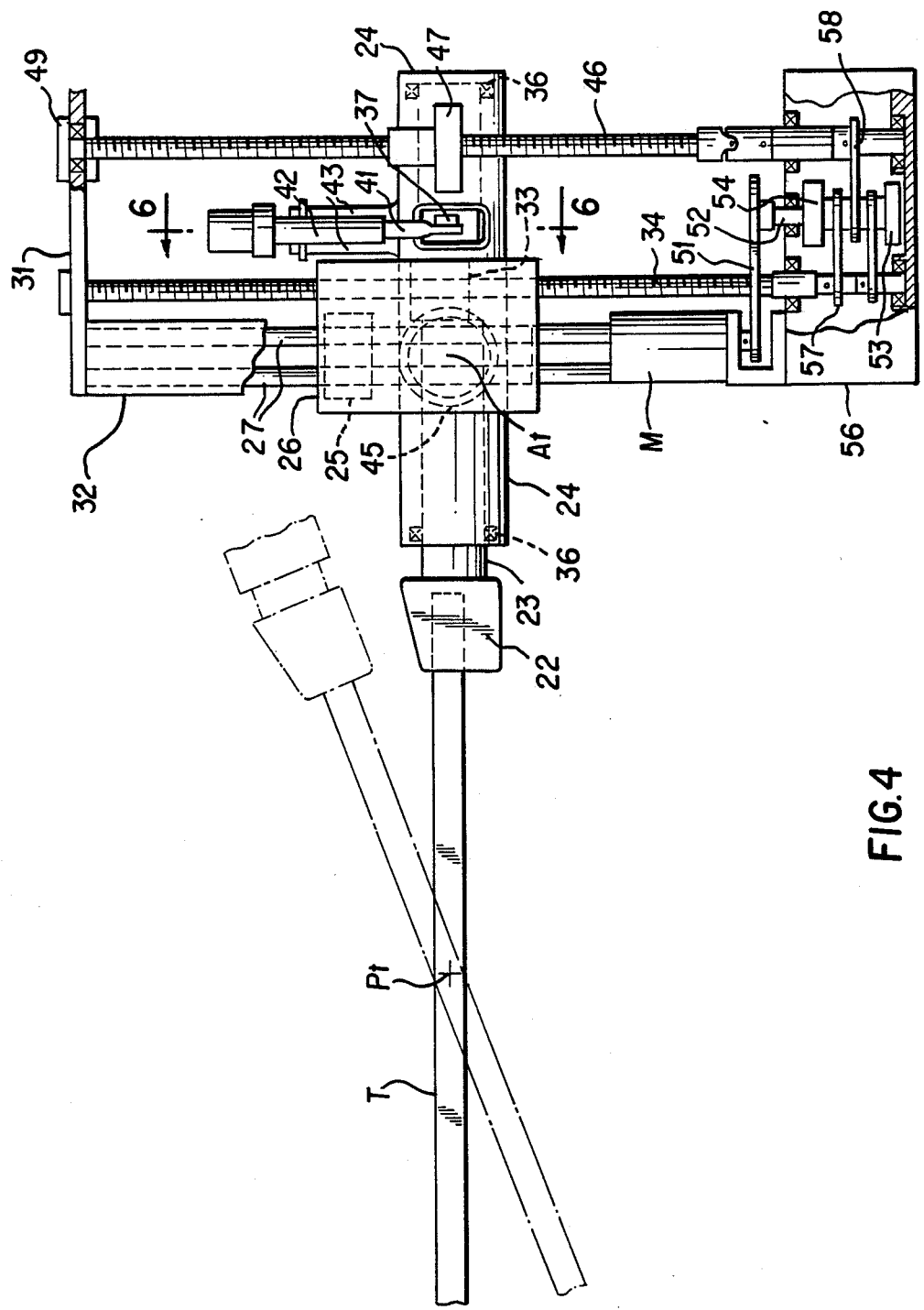
FIG. 4 is an enlarged elevation of the support apparatus from the same side as FIG. 2, showing a drive for tilting the table top of the support.
Figure 5:
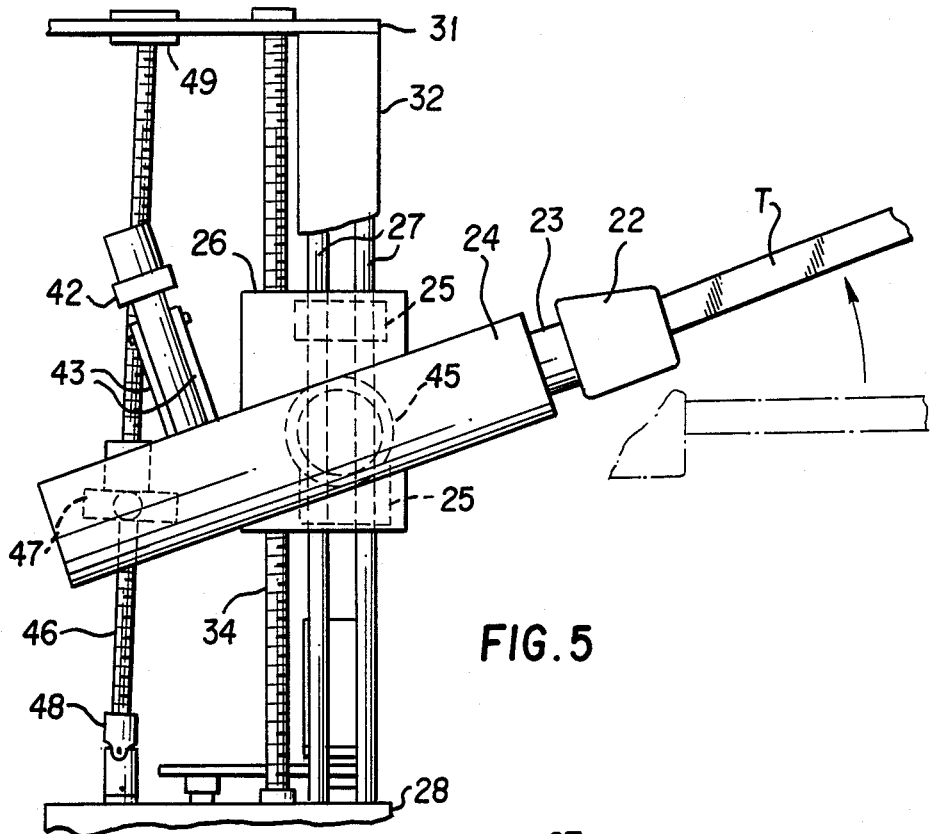
FIG. 5 is an enlarged side elevation of the support apparatus from the opposite side as FIG. 2.
Figure 6:
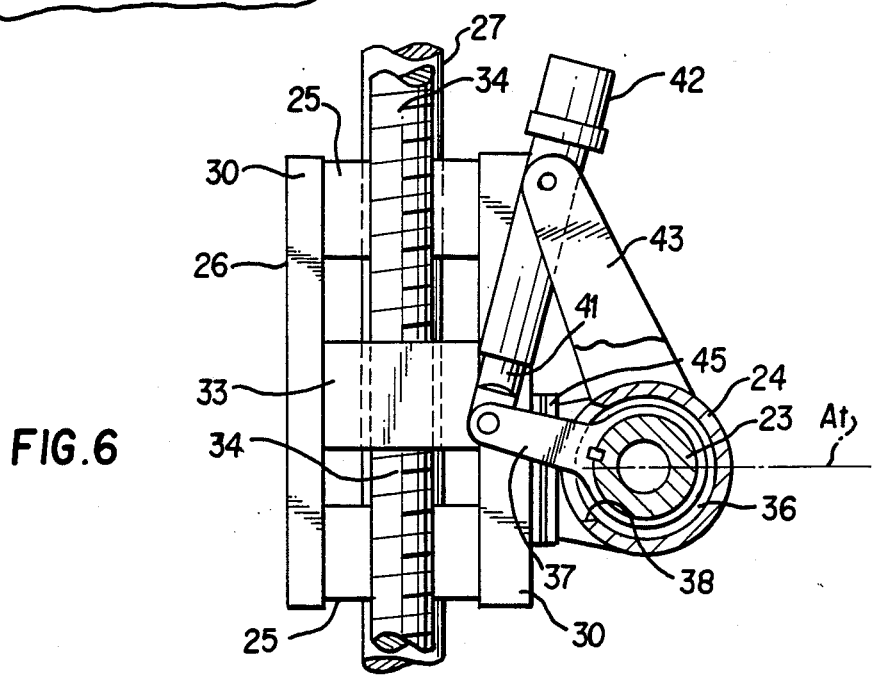
FIG. 6 is a further enlarged side elevation of the drive of FIG. 4 viewed from line 6—6 of FIG. 4.

The table top support mechanism within the housing 20 is shown in FIGS. 3 to 6 wherein the exterior walls 26 surrounding the internal support mechanism have been broken away in FIG. 3 and omitted from FIGS. 4 to 6. A carriage 26 for the table T has between two side plates 30 a linear bearing box 25 riding on vertical rails 27 anchored in a base 28. The upper ends of the rails are set in a top plate 31 supported above the base by two columns 32 of which one is shown in FIGS. 3 and 4 and the other in FIG. 5. Also held between the side plates 30 of the table carriage 26 is a nut 33 whose threads engage a vertical lift screw 34 journalled in the top plate 31 and the base 28 and driven by chains within the base as described more fully with reference to FIG. 4. Rotation of the lift screw 34 raises and lowers the carriage 26 and the table top T connected to the carriage by the lateral arm 22, shaft 23 and tube 24.

The tube 24 has bearings 36 at each end rotatively supporting the shaft 23. A crank arm 37 keyed to the shaft 23 extends out through a window 38 in the bearing tube 24 to the plunger 41 of a linear drive motor 42 supported on the bearing tube 24 by brackets 43. The linear drive may be a linear actuator sold by General Motors Corporation, Saginaw, Michigan, under the trade designation HiTee 90, and its linear movement can be finely controlled by a potentiometer. Rotation of the shaft 23 by the drive 42 cants the table about the shaft axis parallel to the longitudinal axis Al. As described hereinafter the rotation may be centered on the longitudinal axis.

The bearing tube is attached to the lift carriage 26 by a rotary bearing 45 allowing the bearing tube 36 and table T to tilt about an axis At at 90° transverse of the longitudinal table axis Al. Without more the tilting is about the rotary bearing axis, but as explained hereinafter the transverse tilt axis may be located medially of the patient P and table top T by concomitant drive of a second, tilt screw 46 which is engage by a nut 47 fixed on the bearing tube 36 so as to control rotation of the bearing tube 24 about the axis of the rotary bearing 45.

The tilt screw 46 (so called to distinguish it from the lift screw 34 although both screws have lifting and tilting functions) is connected at its lower end to a universal joint 48 driven from within the base 28. The upper end of the tilt screw 46 is journalled in a bearing block 49 sliding in a slot 50 in the top plate 31. Turning the tilt screw 46 rotates the bearing tube 24 about the rotary bearing 45 on the carriage 26. If the lift screw 34 is not turning the tilt screw 46 will tilt the tube 24 and table top T about the axis of the rotary bearing 45. If both screws 34 and 46 are turned at the same speed the bearing tube will not be rotated, but both the tube and table top will be lifted or lowered translationally, that is, without rotation.

It must be anticipated that a patient may go into shock or other trauma during the surgical procedure being monitored radiologically and by the anesthesiologist. The emergency procedures then are to lower the patient's head in the case of shock, or to raise his head in the case of embolism, for example. A special tilting of the patient about a transverse axis through a mid-point Pt of the patient (FIG. 2) is called Trendelenburg rotation when head down and reverse Trendelenburg if head up. As can be seen from the phantom positions of the table top T in FIG. 2 either Trendelenburg rotation simply around the Trendelenburg point Pt raises or lowers the head of the patient.

As in FIGS. 3 and 4 the lift and tilt screws are driven by a reversible motor M linked by a sprocket chain 51 to a drive shaft 52. A first, lift clutch 53 on the shaft, when electrically engaged with the shaft, drives a sprocket chain 56 linked by a pulley to the lift screw 34, an unclutched chain 58 directly links the drive shaft to a pulley on the lift screw 46. These two chain links 56 and 58 have the same speed reduction ratio, and turn the two screws 34 at the same speed thus lifting or lowering the bearing tube 24 without rotation.

For forward, head down Trendelenburg rotations requiring a combination of lowering of the carriage 26 and rotation of the bearing tube, the lift clutch 53 is disengaged and a tilt clutch 54 is engaged with the drive shaft linking a chain 57 with a pulley on the lift screw 34. The chain and pulley link 54 has a greater reduction than for the chain 58 so that the carriage is lowered at a slower rate by the lift screw 34 than the gearing tube 24 is lowered by the tilt screw 46. Consequently the table top T is rotated about the Trendelenburg point to a head down position. For reverse Trendelenburg rotation of the table top to the foot down position in FIG. 4, the motor M is reversed. Thus by the differential drive of the lift and tilt screws Trendelenburg the table top is rotated about its midpoint although the transverse axis of rotation is located beyond and to the side of the table top, leaving the zone beneath the table unobstructed. If the X-ray apparatus is in the zone around the patient and table at the time Trendelenburg rotation is needed, or at any other time, the X-ray tube and receptor may be rotated by longitudinal movement of the ceiling carriage 11 along the horizontal track 12. The X-ray tube and receptor may also be removed from the zone laterally of the table by swinging the carriage on the vertical axis of a pivot 14 of rotary bearings 15 included in its attachment to the track 12.

It should be understood that the present disclosure is for the purpose of illustration only and that this invention includes all modifications and equivalents which fall within the scope of the appended claims.

What is claimed:

1. Patient support apparatus for medical procedures comprising:
    a table top for a patient having a central, longitudinal axis through the head and foot ends of the top;
    a support for the table top including a base and mechanism for moveable support of the table; and
    a support connection between the support mechanism and one end of the table top, the connection extending and joining to the table top at one longitudinal side thereof offset from the longitudinal axis and providing at the supported end of the table top an area of unobstructed access to medical personnel, the apparatus including:
    an arm connected to and extending laterally of the table top at one end thereof;
    a rotating shaft connected to the arm, the shaft being offset from the longitudinal axis of the top and extending from the mechanism on a rotational axis parallel to and offset from the longitudinal axis;
    the shaft being rotatively supported in a vertically moveable carriage to turn about the shaft axis;
    and the carriage includes bearing means mounting the shaft for tilting about an axis parallel to the end of the table and transverse of the end of the shaft axis.

2. Patient support apparatus for medical procedures comprising:
    a table top for a patient having a central, longitudinal axis through the head and foot ends of the top;
    a support for the table top including a base and mechanism for moveable support of the table; and
    a support connection between the support mechanism and one end of the table top, the connection extending and joining to the table top at one longitudinal side thereof offset from the longitudinal axis and providing at the supported end of the table top an area of unobstructed access to medical personnel, the apparatus including:
    an arm connected to and extending laterally of the table top at one end thereof;
    a rotating shaft connected to the arm, the shaft being offset from the longitudinal axis of the top and extending from the mechanism on a rotational axis parallel to and offset from the longitudinal axis;
    the shaft being rotatively supported in a vertically moveable carriage to turn about the shaft axis;
    and the carriage includes bearing means mounting the shaft for tilting about an axis intermediate the ends of the table top.

3. Patient support apparatus for medical procedures comprising:
    a table top for a patient having a central, longitudinal axis through the head and foot ends of the top;
    a support for the table top including a base and mechanism for moveable support of the table; and
    a support connection between the support mechanism and one end of the table top, the connection extending and joining to the table top at one longitudinal side thereof offset from the longitudinal axis and providing at the supported end of the table top an area of unobstructed access to medical personnel, the apparatus including:
    an arm connected to and extending laterally of the table top at one end thereof;
    a rotating shaft connected to the arm, the shaft being offset from the longitudinal axis of the top and extending from the mechanism on a rotational axis parallel to and offset from the longitudinal axis; wherein
    the shaft is rotatively supported in a vertically moveable carriage to turn about the shaft axis and the carriage includes bearing means mounting the shaft for tilting about an axis parallel to the table and transverse of the shaft axis.

4. Patient support apparatus for medical procedures comprising:
    a table top for a patient having a central, longitudinal axis through the head and foot ends of the top;
    a support for the table top including a base and mechanism for moveable support of the table; and
    a support connection between the support mechanism and one end of the table top, the connection extending and joining to the table top at one longitudinal side thereof offset from the longitudinal axis and providing at the supported end of the table top an area of unobstructed access to medical personnel, and wherein the apparatus includes:
    an arm connected to and extending laterally of the table top at one end thereof;
    a rotating shaft connected to the arm, the shaft being offset from the longitudinal axis of the top and extending from the mechanism on a rotational axis parallel to and offset from the longitudinal axis;
    the shaft is rotatively supported in a vertically moveable carriage to turn about the shaft axis;
    the apparatus includes vertical tracks for the carriage and motor means to move the carriage along the tracks; and the carriage includes bearing means mounting the shaft for tilting about an axis parallel to the plane of the table and transverse of the shaft axis, and the motor means includes a lift screw and a second screw moving the carriage vertically.

5. Apparatus according to claim 4 wherein the motor means has a differential coupling to the lift and second screws to drive them at different speeds and tilt the table about a transverse axis centrally of the table.

* * * * *